United States Patent [19]

Myers et al.

[11] Patent Number: 5,011,481
[45] Date of Patent: Apr. 30, 1991

[54] HOLDER FOR ANNULOPLASTY RING

[75] Inventors: David J. Myers, Garden Grove; Richard Leever, Pomona; Mary Gibbs, Garden Grove, all of Calif.; John T. M. Wright, Conifer, Colo.

[73] Assignee: Medtronic, Inc., Minneapolis, Minn.

[21] Appl. No.: 380,345

[22] Filed: Jul. 17, 1989

[51] Int. Cl.$^5$ ............................................. A61F 2/24
[52] U.S. Cl. .......................................... 606/1; 623/2
[58] Field of Search ................................ 623/2; 606/1

[56] References Cited

U.S. PATENT DOCUMENTS

| | | | |
|---|---|---|---|
| 4,042,979 | 8/1977 | Angell | 3/1.5 |
| 4,055,861 | 11/1977 | Carpentier et al. | 3/1.5 |
| 4,217,665 | 8/1980 | Bex et al. | 3/1.5 |
| 4,290,151 | 9/1981 | Massana | 3/1.5 |
| 4,489,446 | 12/1984 | Reed | 3/1.5 |
| 4,585,453 | 4/1986 | Martin et al. | 623/2 |
| 4,602,911 | 7/1986 | Ahmadi et al. | 623/2 |
| 4,865,600 | 9/1989 | Carpentier et al. | 623/2 |

FOREIGN PATENT DOCUMENTS

| | | | |
|---|---|---|---|
| 0200419 | 11/1986 | European Pat. Off. | 623/2 |
| 3614292 | 11/1987 | Fed. Rep. of Germany | 623/2 |
| 207339 | 2/1968 | U.S.S.R. | 623/2 |

OTHER PUBLICATIONS

Brochure Entitled "Conservative Repair of Mitral and Tricuspid Valves", by Garcia-Rinaldi et al., Published by Baylor College of Medicine.
Brochure Entitled "Instructions for Use of the Handle/-Holder Assembly for the Carpentier-Edwards Mitral Bioprosthesis", Published by American Edwards Laboratories.
Blueprint Drawing No. 1100291, Dated 4-19-78 entitled "Holder, Ring, Annuloplasty, 22 mm", Hancock Laboratories, Inc.

Primary Examiner—Randall L. Green
Assistant Examiner—Gary Jackson
Attorney, Agent, or Firm—Reed A. Duthler

[57] ABSTRACT

A surgical tool to assist in handling and implantation of flexible annuloplasty rings. The holder takes the form of an oblate ring to which the annuloplasty ring is mounted. The annuloplasty ring is retained on the holder by means of radially extending fingers and sutures.

14 Claims, 1 Drawing Sheet

HOLDER FOR ANNULOPLASTY RING

BACKGROUND OF THE INVENTION

The present invention relates generally to surgical tools and more particularly for surgical tools used in conjunction with annuloplasty rings.

Annuloplasty rings are useful in a variety of surgical procedures, including mitral and tricuspid annular reduction. In these procedures, sutures are first placed around the valve annulus at spaced intervals. Sutures passing through the annulus in the intertrigonal area are spaced equidistant from one another, for example, at 2 mm intervals. Sutures passing through the annulus around the remainder of the valve are typically spaced at somewhat wider intervals, for example, 4 mm. The sutures surrounding the valve annulus are then brought through the annuloplasty ring. The sutures passing through the annulus between the trigones are passed through the annuloplasty ring with the same spacing, for example, 2 mm. The remainder of the sutures are passed through the annuloplasty ring more closely spaced than where they pass through the annulus, for example, 1½ mm. The process of passing the sutures through the ring occurs while the ring is held above the valve annulus. The ring is then moved down into contact with the valve annulus, causing contraction of the annulus with the exception of the intertrigonal area, thus effecting a reduction in valve annulus circumference. This basic procedure is used to correct both mitral and tricuspid annular dilatation.

In order for the sutures to be passed through the annuloplasty ring, it is desirable that the ring be held in a fixture or tool of some fashion. One available tool is manufactured by Pilling Instruments, and takes the general form of a cone provided with a circumferential groove near the base. The cone is also provided with longitudinal slits, so that the tool may be contracted to accept the ring around the circumference of the groove. The tool is adapted to be held by means of a threaded handle.

SUMMARY OF THE INVENTION

The present invention is directed toward an improved holder for use with annuloplasty rings. The holder is specifically configured to assist the surgeon in performing the technique of mitral or tricuspid reduction, and is intended to be provided in conjunction with the annuloplasty ring, ready for use. The ring holder takes the general form of an oblate ring member having an outer circumference equal to the inner circumference of the annuloplasty ring with which it is used. The outer circumference of the holder member comprises two arcuate segments joined at their ends, the radius of curvature of one of the arcuate segments being significantly smaller than the other.

Along each of the arcuate segments are a plurality of radially extending fingers which engage the annuloplasty ring, without unduly obstructing access to the ring. A plurality of the fingers are provided with suture bores perpendicular to and peripherally spaced from the ring. Corresponding inwardly placed suture bores in the holder member allow for the use of sutures to retain the annuloplasty ring on the holder. The holder is also provided with a centrally located receiving member having a threaded bore, allowing the holder to be used in conjunction with a threaded handle.

The ring is intended to be mounted to the ring holder such that markers placed on the rings, corresponding to the location of the trigones on the valve, are placed along the arcuate segment of the holder having the greater radius of curvature. Radially extending fingers located between the trigone markers are located at first, evenly spaced intervals, while the fingers around the periphery of the rest of the holder are more widely spaced. The spacing of the fingers assists the physician both in assuring that sutures are evenly spaced and that the sutures are at proper intervals around the ring.

DETAILED DESCRIPTION OF THE INVENTION

Figure 1:
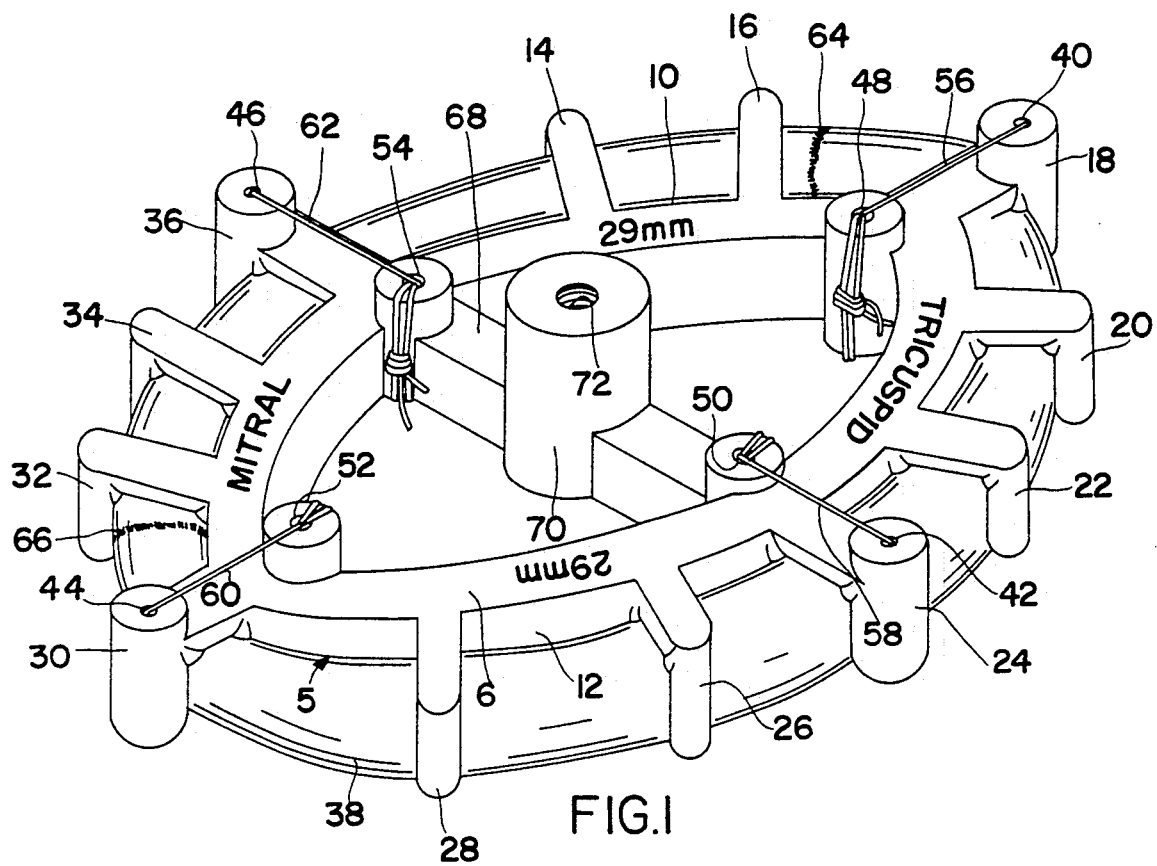
FIG. 1 is a perspective view of a ring holder according to the invention, with the annuloplasty ring mounted thereto.

FIG. 1 is a perspective view from above of the annuloplasty ring holder, with the annuloplasty ring attached. This is the configuration in which it is anticipated that the two products will be provided to the physician for use. The outer periphery of the holder member 5 generally comprises two arcuate segments 10 and 12 which define a generally planar oblate ring having upper surface 6 and an opposite, lower surface. The radius of curvature of segment 10 is substantially greater than the radius of curvature of segment 12. Annuloplasty ring 38 is mounted around the external circumferential surface 7 of holder member 5. Spaced around holder member 5 are a plurality of retaining fingers 14, 16, 18, 20, 22, 24, 26, 28, 30, 32, 34 and 36. Each of the fingers includes a radially extending portion which extends across the annuloplasty ring 38 and a vertically extending portion, located radially outward of ring 38. These fingers, in conjunction with the arcuate segments 10 and 12 serve to retain the ring 38 on the ring holder.

Fingers 18, 24, 30 and 36 are provided with suture bores 40, 42, 44 and 46, respectively, which pass through the vertically extending portions of the fingers. The holder member 5 is also provided with a plurality of perpendicular suture bores 48, 50, 52 and 54, located radially inward of ring 38 across from suture bores 40, 42, 44 and 46, respectively. As illustrated, sutures 56, 58, 60 and 62 are passed through the suture bores and around annuloplasty ring 38, and serve to retain annuloplasty ring 38 on the ring holder during the surgical procedure. It should be noted that fingers 18, 24, 30 and 36 are each provided with a portion which extends vertically above the upper surface 6 of the holder member 5. Suture bores 40, 42, 44 and 46 are located in these vertically extending portions of the fingers. Correspondingly, suture bores 48, 50, 52 and 54 are located in portions of the holder member 5 which also extend vertically above the upper surface 6 of holder member 5. This results in the portions of the sutures 56, 58, 60 and 62 which cross the upper surface 6 of the ring member 5 being spaced from the upper surface 6, facilitating the use of a scalpel or other cutting tool to sever the sutures and release the annuloplasty ring 38. Sutures 56, 58, 60 and 62 should be tied to holder member 5 so that after they are cut, they remain attached to the holder member 5.

It should be noted that the trigonal markers 64 and 66 are located along arcuate segment 10, between fingers 16 and 18 and between fingers 30 and 32. Fingers 32, 34, 36, 14 and 16, located between trigonal markers 64 and 66 are evenly spaced from one another at their radial extremities. Similarly, fingers 16, 18, 20, 22, 24, 26, 28 and 32 are evenly spaced from one another at their radial extremities. However, the spacing between fingers 26 and 28, for example, is significantly greater than the spacing between fingers 14 and 16.

As noted above, during mitral or tricuspid annular reduction, the spacing of the sutures between the trigonal markers 64 and 66 is intended to be different from that between sutures surrounding the rest of the annuloplasty ring. The fact that the fingers are evenly spaced within each of these regions of the ring facilitates even spacing of the sutures by the physician. The fact that the fingers are differentially spaced along these two regions assists in reminding the physician that the spacing of the sutures should be spaced differently between the trigonal markers than around the rest of the ring.

Located centrally to the holder member is a receiving member 68 which includes a central, cylindrical portion 70, provided with a threaded bore 72. A threaded handle may thus be inserted into bore 72 to facilitate use of the ring holder. The cylindrical portion 70 extends vertically above the portions of the ring member 5 in which the suture bores are located so that a locking nut may be used in conjunction with the threaded handle without interfering with access to the sutures 56, 58, 60 and 62. Threaded bore 72 is dead-ended, so that a threaded handle may be inserted only from one direction.

As illustrated in FIG. 1, adjacent arcuate segment 10, the holder member 5 bears the marking "MITRAL 29 mm", while adjacent arcuate segment 12 is the marking "TRICUSPID 29 mm". These markings are intended as an aid to the physician. These markings presume that access to the mitral valve will be made by means of an atrial left atriotomy. In this case, the labeling "MITRAL 29 mm" will be generally upright in the physician's field of vision when the trigone markers 64 and 62 are properly oriented with respect to the trigones of the valve. Similarly, assuming that access to the tricuspid valve is made by means of a longitudinal right atriotomy, the trigone markers 64 and 66 will be generally in their proper locations with respect to the trigones of the valve when the label "TRICUSPID 29 mm" is upright in the physician's field of vision. This feature is believed to assist in initial proper orientation of the ring and holder during the surgical procedure.

Figure 2:
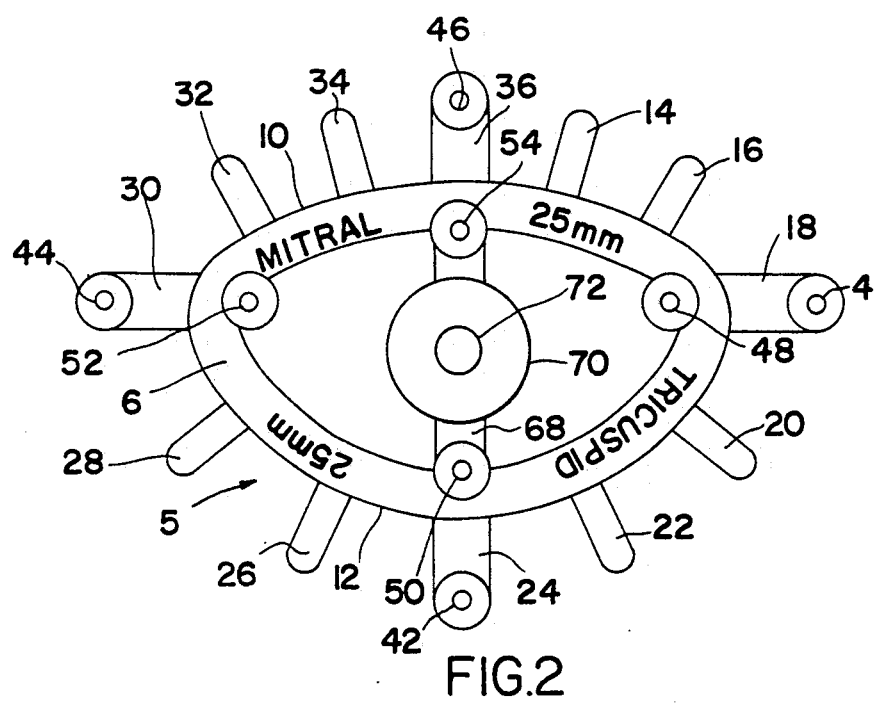
FIG. 2 is a top plan view of the annuloplasty ring holder.

FIG. 2 is a top, plan view of the holder illustrated in FIG. 1. In this view, the spacing between the radially extending fingers and the different arcs of curvature of the two arcuate segments are more clearly visible. As can be seen, arcuate segment 10 has a substantially greater radius of curvature than arcuate segment 12. In this view, it is also apparent that the spacing between the radial extremities of fingers 32, 34, 36, 14 and 16 is relatively even, and less than the spacing between the radial extremities of fingers 18, 20, 22, 24, 26, 28 and 30.

In use, marks on the annuloplasty ring signifying the location of the trigones will fall between fingers 30 and 32 and between fingers 16 and 18. All other structures marked in FIG. 2 correspond to identically marked structures in FIG. 1.

The annuloplasty ring 38 illustrated in FIGS. 1 and 2 is a Duran TM flexible annuloplasty ring, marketed by Medtronic, Inc. While the specific configuration illustrated is optimized for use with the Duran TM annuloplasty ring, the holder of the present invention is believed also adaptable for use in conjunction with other flexible and rigid annuloplasty rings, including those disclosed in Carpentier et al U.S. Pat. No. 4,055,861, Reed U.S. Pat. No. 4,489,446, Angel U.S. Pat. No. 4,042,979 and Bex et al U.S. Pat. No. 4,217,665. While the configuration of the external periphery of the holder may have to be varied in order to adapt the holder for use with some of these other rings, it is believed within the scope of the invention to do so.

The Duran TM annuloplasty ring is a ring which is both flexible and slightly elastic. Typically, the ring may be circumferentially elongated up to about 10% of its circumference. The ring is also resilient. For rings of this type, it is desirable that the annuloplasty ring fit snuggly around the circumference of the ring holder member 5 without substantial elongation. A snug fit is desirable to prevent looping or pulling away of the ring from the holder member during the suturing procedure as the sutures are pulled through the ring. While the fit should be snug, it should not result in any significant circumferential elongation of the ring, as this may encourage the ring to take a permanent set.

The holder illustrated in FIGS. 1 and 2 is intended to be an example of one of a family of products, covering a range of sizes. Each annuloplasty ring of the type illustrated is provided with three equidistantly spaced markers, two of which correspond to markers 52 and 64 (FIG. 1) and are intended to correspond to the location of the trigones of the patient's valve. The distance between two adjacent markers on the annuloplasty ring is the size designation. For example, in the annuloplasty ring illustrated in FIG. 1, the lineal distance along the ring 38 between marker 52 and marker 64 is 29 mm. Flexible annuloplasty rings of this type are generally available in sizes from 25 mm to 35 mm. As such, the spacing between the fingers on the variously sized ring holders will vary somewhat. It is also anticipated that the number of fingers and the number of fingers which carry suture bores may also be varied, although the configuration illustrated in FIG. 2, in which the four suture bores are located in fingers displaced approximately 90° from one another, is believed to be the preferred configuration. The illustrated embodiment of the ring holder is intended to be merely exemplary, and not limiting with regard to the following claims.

In conjunction with the above specification, we claim:

1. A holder for an annuloplasty ring, comprising: a holder member having an outer circumferential surface, said member provided with a plurality of fingers extending radially from said member, said fingers each comprising a segment extending radially from said holder member and a segment perpendicular to said radially extending segment and spaced radially outward of said outer circumferential surface, whereby an annuloplasty ring may be inserted between said circumferential surface and said perpendicular segments of said fingers.

2. A holder according to claim 1 wherein said plurality of fingers includes a first plurality of fingers spaced from one another at a first interval, and a second plurality of fingers spaced from one another at a second interval differing from said first interval.

3. A holder according to claim 2 wherein the outer circumference of said holder member comprises first and second arcuate segments, said first arcuate segment having a radius of curvature substantially greater than said second arcuate segment.

4. A holder according to claim 3 wherein said first plurality of fingers are located along a portion of said first arcuate segment and wherein said second plurality of fingers are located along said second arcuate segment.

5. A combination holder and annuloplasty ring for use by a surgeon in conjunction with annuloplasty surgery performed on a patient's heart valve, comprising:
an annuloplasty ring having an inner circumference and an outer circumference;
a holder member having an outer circumference corresponding to the inner circumference of said annuloplasty ring, said annuloplasty ring mounted around said member, said holder member provided with a plurality of fingers, each of said fingers including a portion extending radially across said annuloplasty ring and a portion generally perpendicular to the plane of said radially extending portion and engaging said annuloplasty ring around its exterior circumference.

6. An annuloplasty ring and holder according to claim 5 wherein said plurality of fingers comprise a first plurality of fingers spaced at first intervals from one another and a second plurality of fingers spaced at second intervals from one another around said holder member.

7. An annuloplasty ring and holder according to claim 6 wherein the outer circumference of said holder member comprises first and second arcuate segments, said first arcuate segment having a greater radius of curvature than said second arcuate segment.

8. An annuloplasty ring and holder according to claim 7 wherein said first plurality of fingers are located along said first arcuate segment and wherein said wherein said second plurality of fingers are located along said second arcuate segment.

9. An annuloplasty ring and holder according to claim 8 wherein said annuloplasty ring is provided with first and second markers indicating the desired position of the annuloplasty ring with regard to the trigones of the patient's valve, wherein said first and second markers are located adjacent said first arcuate segment, and wherein said first plurality of radially extending finger are located along said first arcuate segment, intermediate said first and second markers.

10. An annuloplasty ring and holder according to claim 9 wherein said holder member is provided with orientation indicative markings, including first indicia indicating that said first arcuate segment should be placed uppermost in said surgeon's field of vision when said annuloplasty ring is used on said patient's mitral valve and second indicia indicating that said second segment should be uppermost in said surgeon's field of vision when said holder is used in conjunction with said patient's tricuspid valve.

11. An annuloplasty ring and holder according to claim 5 wherein a plurality of said fingers are provided with suture bores extending through said vertical portions of said fingers, and wherein said annuloplasty ring is further retained on said holder by means of sutures passing around said annuloplasty ring, through said suture bores in said fingers.

12. An annuloplasty ring and holder according to claim 11 wherein said holder member is provided with a plurality of suture bores, each suture bore is said holder member located across said annuloplasty ring from one of said suture bores in said fingers, said sutures each passing through a suture bore in one of said radially extending fingers and through a suture bore located on said holder member.

13. An annuloplasty ring and holder according to claim 12 wherein said vertical portions of those of said fingers which are provided with suture bores extend vertically above said holder member and wherein the portions of said member in which said suture bores in said holder member are located also extend vertically above said holder member, whereby said sutures are also spaced from said holder member between the vertically extending portions of said member and said fingers, facilitating cutting of said sutures to release said annuloplasty ring.

14. An annuloplasty holder and ring according to claim 13 wherein said holder member is further provided with a receiving member having a threaded bore, said receiving member also extending vertically above said holder member.

* * * * *